(12) United States Patent
Mo et al.

(10) Patent No.: US 6,312,385 B1
(45) Date of Patent: Nov. 6, 2001

(54) METHOD AND APPARATUS FOR AUTOMATIC DETECTION AND SIZING OF CYSTIC OBJECTS

(75) Inventors: Larry Y. L. Mo, Waukesha; Fang Dong, Middleton, both of WI (US)

(73) Assignee: GE Medical Systems Global Technology Company, LLC, Milwaukee, WI (US)

( * ) Notice: Subject to any disclaimer, the term of this patent is extended or adjusted under 35 U.S.C. 154(b) by 0 days.

(21) Appl. No.: 09/563,538

(22) Filed: May 1, 2000

(51) Int. Cl.$^7$ ............................................ A61B 8/00
(52) U.S. Cl. ................................. 600/443; 600/447
(58) Field of Search ............................... 600/443, 447, 600/444, 449, 445, 450, 437

(56) References Cited

U.S. PATENT DOCUMENTS

| | | | |
|---|---|---|---|
| 5,056,146 | * 10/1991 | Nishide | 382/2 |
| 5,215,093 | * 6/1993 | Miyazaki et al. | 600/445 |
| 5,469,850 | * 11/1995 | Iizuka et al. | 600/443 |
| 5,588,435 | * 12/1996 | Weng et al. | 600/443 |

* cited by examiner

Primary Examiner—Marvin M. Lateef
Assistant Examiner—Maulin Patel
(74) Attorney, Agent, or Firm—Peter J. Vogel; Dennis M. Flaherty

(57) ABSTRACT

Method and apparatus for automatically detecting and sizing cystic objects in ultrasound imaging. The cystic objects can be automatically detected by the steps of reading an image frame from memory; defining a search region within the image frame or a decimated version of the image frame; binarizing the pixel values within the search region based on a pixel value threshold that is adaptive to local pixel value statistics; morphological filtering the binarized pixel values to eliminate structures smaller than the speckle size; counting the number of continuous objects and keeping track of their area; and rejecting objects that are outside a predetermined size range. Each detected cystic object is automatically sized and graphical information representing the results of the automatic sizing process may be displayed.

42 Claims, 5 Drawing Sheets

METHOD AND APPARATUS FOR AUTOMATIC DETECTION AND SIZING OF CYSTIC OBJECTS

FIELD OF THE INVENTION

This invention generally relates to ultrasound imaging of tissue. In particular, the invention relates to systems and methods for automatically sizing tissue structures based on an image of the structure.

BACKGROUND OF THE INVENTION

During clinical ultrasound examinations, the sonographer often needs to measure the size of any cystic object seen in images of soft tissues such as a uterus, liver or breast. With conventional scanners, this requires the sonographer to manually locate the cyst and then measure the lengths of its long and short axes. For multiple cysts, it takes a considerable amount of time and effort to measure their sizes one by one. Therefore, a system that automatically locates cystic objects and measures their sizes would improve both patient throughput and measurement consistency.

U.S. Pat. No. 5,588,435 describes a method that automatically measures fetal body structures, such as femur length, humerus length and head circumference. This technique is suitable for use in obstetrical/gynecological applications, and measures multiple objects one at a time. The user also needs to specify one or two initial points on the object by manual control.

There is a need for a method of automatically detecting and sizing other types of tissue structures, in particular, cystic objects. Preferably, such a technique would not require the user to select any initial point. Instead, the whole process from selection of a search region to marking and measuring the cystic area would be automatic.

SUMMARY OF THE INVENTION

The present invention is directed to a method and an apparatus for automatically detecting and sizing cystic objects in ultrasound imaging. Since cystic objects are seen in a wide range of clinical applications, the invention is expected to produce significant productivity enhancements. The performance of the inventive method is optimized when the hypoechoic objects have clearly defined boundaries.

The method in accordance with the preferred embodiment comprises the following steps: (a) reading an image frame from memory; (b) defining a search region within the image frame or a decimated version of the image frame; (c) binarizing the pixel values within the search region based on a pixel value threshold that is adaptive to local pixel value statistics; (d) morphological filtering the binarized pixel values to eliminate structures smaller than the speckle size; (e) counting the number of continuous objects and keeping track of their area; and (f) rejecting objects that are outside a predetermined size range. As a result of this method, cystic objects in an image can be detected automatically.

In accordance with the preferred embodiment, each detected cystic object is automatically sized and graphical information representing the results of the automatic sizing process may be displayed. Automatic sizing is accomplished by finding the center of mass of each remaining object, and then measuring the major and minor axes of each remaining object relative to its center of mass.

DETAILED DESCRIPTION OF THE PREFERRED EMBODIMENTS

Figure 1:
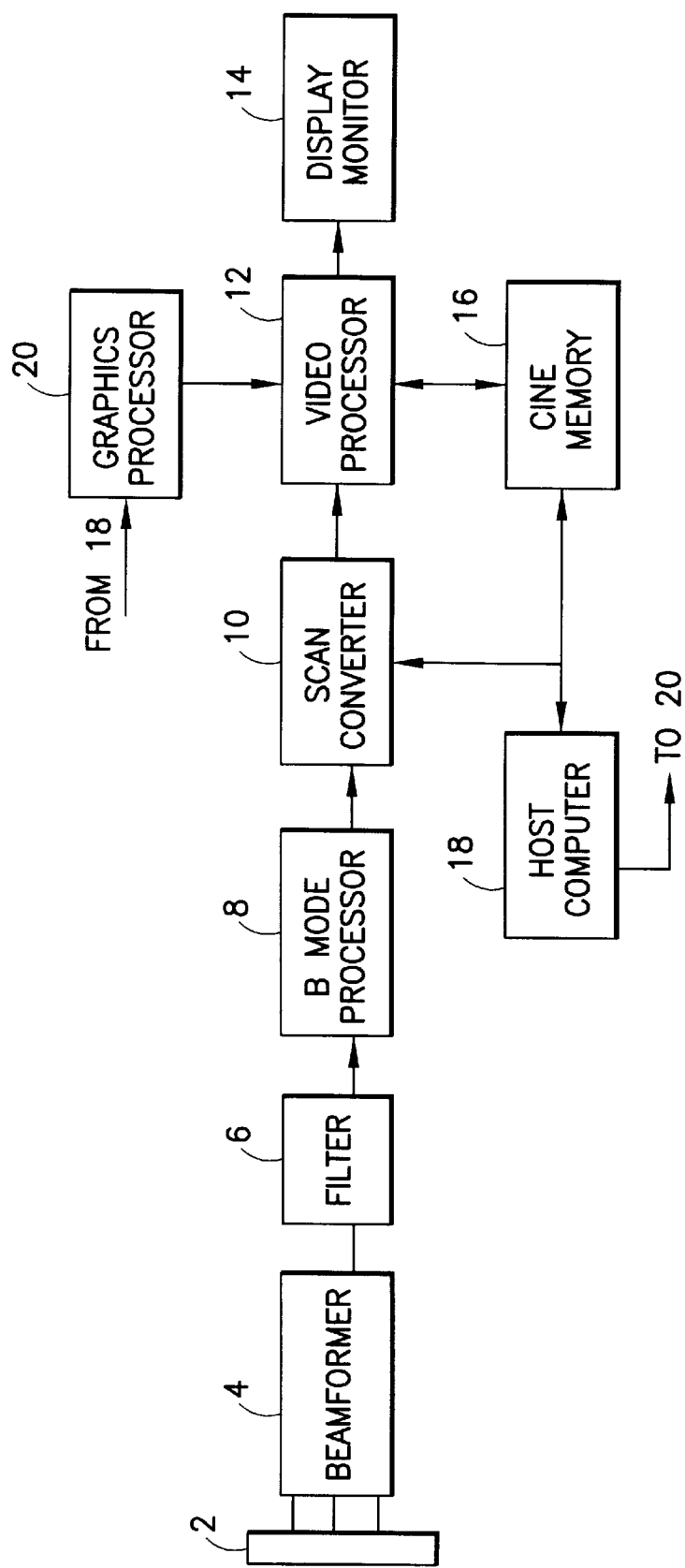
FIG. 1 is a block diagram showing the general architecture of an ultrasound imaging system having B-mode imaging.

One conventional ultrasound imaging system is generally depicted in FIG. 1. The main data path begins with the analog RF inputs to the beamformer 4 from the transducer 2. The beamformer 4 is responsible for the transmit and receive beamforming. The beamformer's signal inputs are the low-level analog RF signals from the transducer elements. The beamformer further comprises a complex bandpass filter which outputs two summed digital in-phase (I) and quadrature (Q) receive beams formed from acquired data samples. These data samples are derived from the reflected ultrasound from respective focal zones of the transmitted beams. The complex bandpass filters are programmed with filter coefficients to pass a band of frequencies centered at a desired frequency, e.g., the fundamental frequency $f_o$ of the transmit waveform or a (sub)harmonic frequency thereof. The beamformer output I and Q data is sent to filters 6, which can reshape the signal spectrum and reject out-of-band noise.

The image data output from the filters 6 is sent to a B-mode processor 8, which converts the I and Q data from the beamformer 4 into a log-compressed version of the time-varying amplitude of the signal envelope. The envelope amplitude of a complex signal is the magnitude of the vector which I and Q represent. The I,Q phase angle is not used in the B-mode display. The magnitude of the signal is the square root of the sum of the squares of the orthogonal components, i.e., $(I^2+Q^2)^{1/2}$. The B-mode amplitude, i.e., intensity, data is output to a scan converter 10. Although the preferred embodiment is disclosed here in the context of a complex bandpass system, the present invention also has application in systems which detect the envelope of the RF signal without the intermediate steps of converting the RF signal to in-phase and quadrature components.

The scan converter 10 accepts the processed B-mode intensity data, interpolates where necessary, and converts the intensity data into X-Y format for video display. In particular, the scan converter 10 performs the coordinate transformation of the B-mode data from polar coordinate (R-θ) sector format or Cartesian coordinate linear format to appropriately scaled Cartesian coordinate display pixel data, which is stored in an X-Y display memory (not shown).

The scan-converted frames are passed to a video processor 12, which maps the video data to a gray-scale mapping for video display. A conventional ultrasound imaging system typically employs a variety of gray maps, which are simple transfer functions of the raw image data to display gray levels. The gray-scale image frames are then sent to the display monitor 14 for display.

The B-mode images displayed by monitor 14 are produced from an image frame of data in which each datum indicates the intensity or brightness of a respective pixel in the display. An image frame may, e.g., comprise a 400×500 data array in which each intensity datum is an 8-bit binary number that indicates pixel brightness. Each pixel has an intensity value which is a function of the backscatter cross section of a respective sample volume in response to interrogating ultrasonic pulses and the gray map employed. The displayed image represents the tissue and/or blood flow in a plane through the body being imaged.

Successive frames of B-mode data are stored in a cine memory 16 on a first-in, first-out basis. Storage can be continuous or as a result of an external trigger event. The cine memory 16 is like a circular image buffer that runs in the background, capturing image data that is displayed in real time to the user. When the user freezes the system by operation of an appropriate device on an operator interface (not shown), the user has the capability to view image data previously captured in cine memory.

System control is centered in a host computer (i.e., master controller) 18, which accepts operator inputs through an operator interface (e.g., a control panel) and in turn controls the various subsystems. The host computer 18 performs system level control functions. It accepts inputs from the operator via the operator interface as well as system status changes (e.g., mode changes) and makes appropriate system changes. A system control bus (not shown) provides the interface from the host computer to the subsystems.

The conventional system has the capability to superimpose graphical symbols on any ultrasound image. The superimposition of graphics on the image frame is accomplished in the video processor 12, which receives the ultrasound image frame from the X-Y display memory in the scan converter 10 and the graphics data from a graphics processor 20. The graphics processor 20 generates data corresponding to graphical symbols to be displayed in the image frame in response to instructions from the host computer 18.

Figure 2:
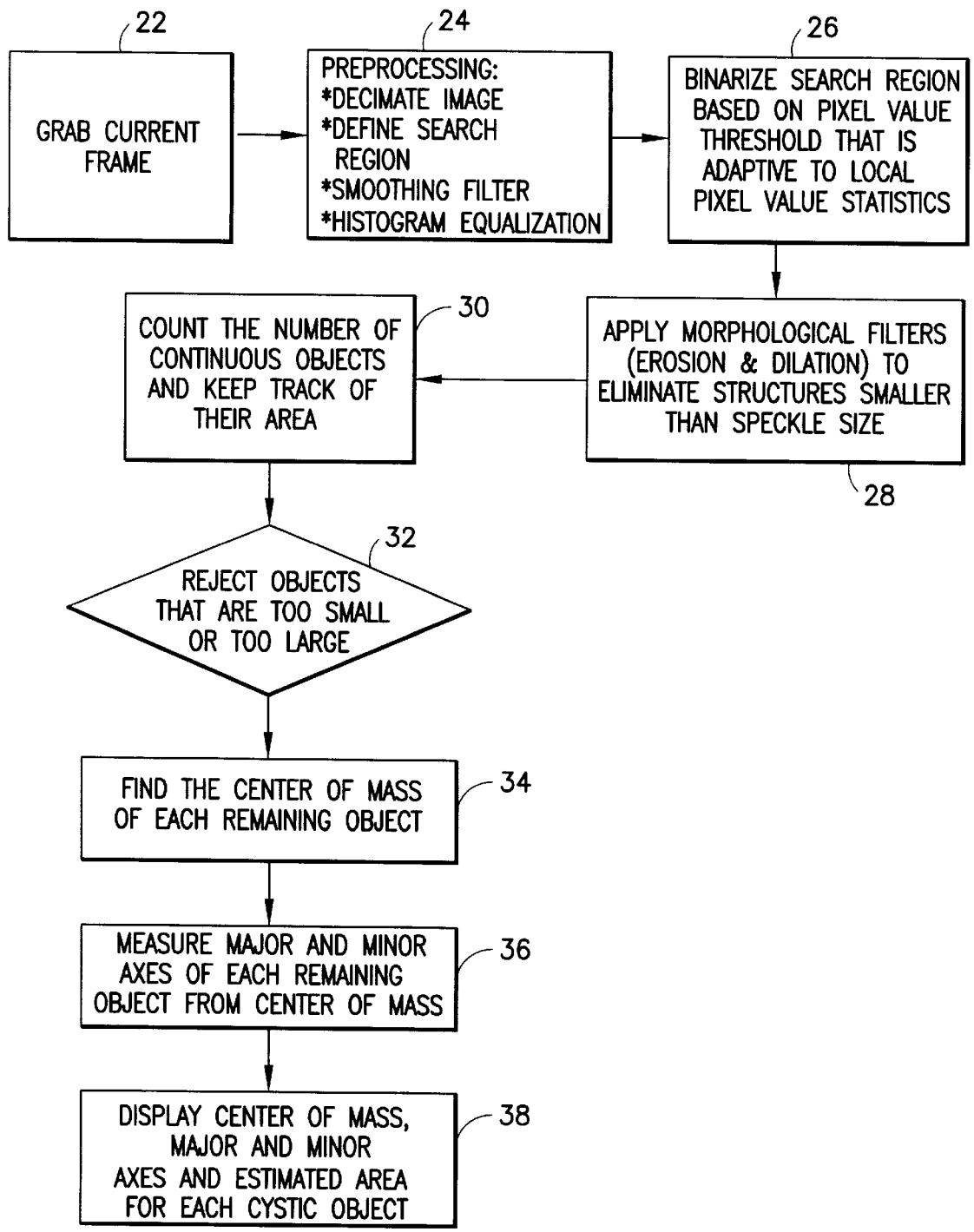
FIG. 2 is a flowchart showing an algorithm for automatic detection and sizing of cysts in accordance with the preferred embodiment of the invention.

The method in accordance with the preferred embodiment of the invention is shown in FIG. 2. In conventional scanners, the current image frame can be read (step 22) either from the X-Y display memory in the scan converter or from the cine memory. To facilitate the cyst detection process, the image is first subject to some preprocessing (step 24), which may include any or all of the following: (1) image decimation to reduce the image to a smaller two-dimensional array of pixel elements; (2) definition of a search region within the decimated image; (3) application of a smoothing filter (e.g., median or mean filter) to reduce speckle noise; and (4) pixel intensity histogram equalization to enhance contrast between background and cyst. The image decimation factor (e.g., 2) is in general dependent on a predefined minimum cyst size and the image size (in terms of pixel count) for the current image depth setting.

Figure 3:
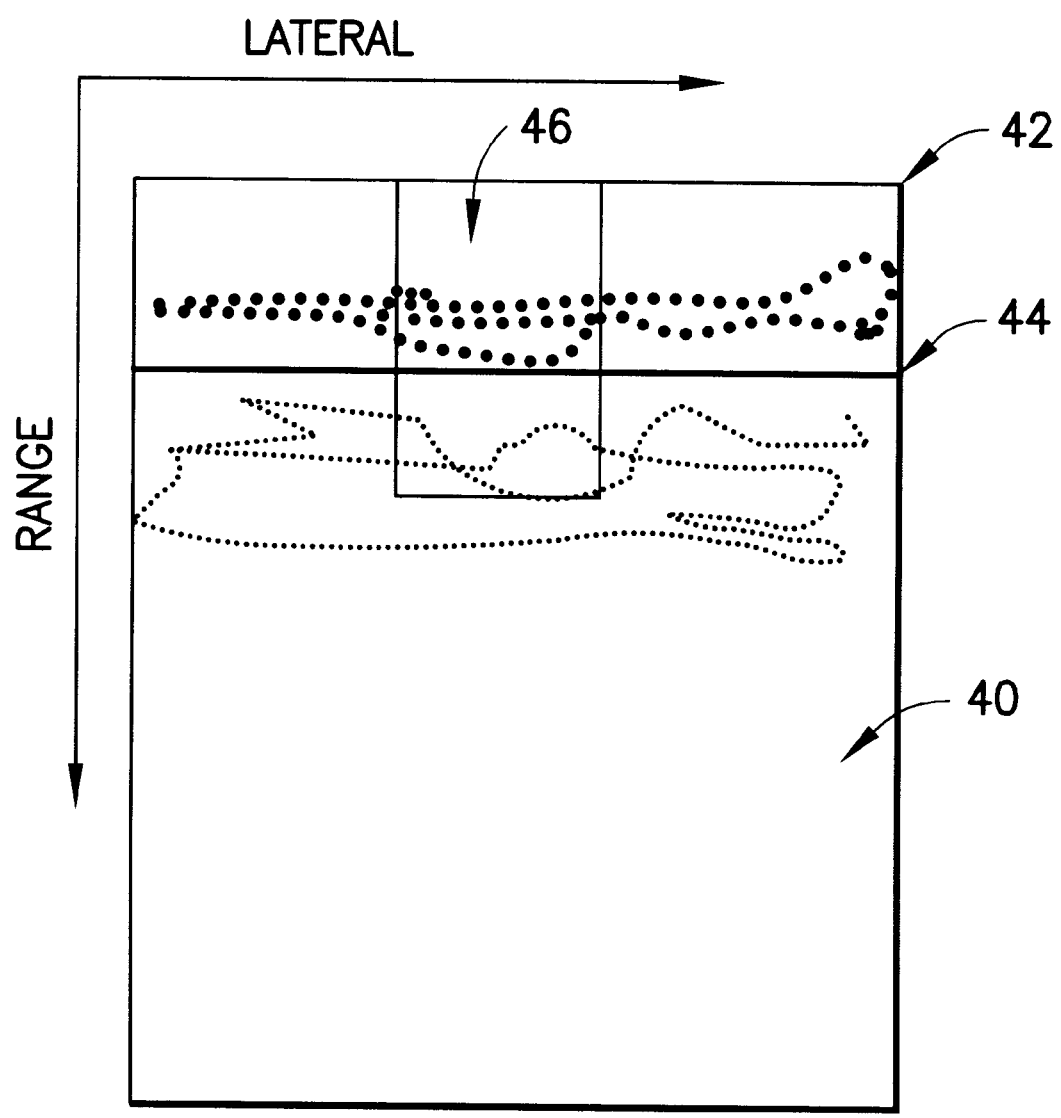
FIG. 3 is a schematic showing a technique for redefining the upper boundary of the search region to exclude near-field reverberation noise in accordance with the preferred embodiment of the invention.

The initial search region may be pre-defined as, e.g., the central 90% of the image frame (after decimation). To minimize the cyst detection processing time, it is advantageous to further exclude an upper band that may be corrupted by near-field reverberation. As an option, the user can select the final search region by putting two cursors at the opposite corners of a desired rectangular search region. However, the preferred method is to perform some simple test for reverberation noise in a small upper region of the search region, as follows:

(a) Define a small box 46 by, e.g., selecting a height corresponding to the top ⅓ of the initial search region 40 in the range direction and a width equal to the central ⅓ of the search region in the lateral direction, as shown in FIG. 3.

(b) Apply an edge detection filter along the range (Y) direction (within the small box only). The simplest example that may suffice is an FIR filter having filter coefficients [1,−1].

(c) Detect pixel values above a predefined threshold. In FIG. 3, the heavy dots represent the bright and sharp reverberation structures after edge detection filtering. The lighter dots represent tissue edges (if any) that are probably less sharp.

(d) compute the mean of the Y-coordinates of all the detected points inside the small box. The Y-position of the estimated mean is indicated by the bold horizontal line 44, while horizontal line 42 indicates the original upper boundary of the search region.

(5) Redefine the upper boundary of the search region as being the bold line 44, which should exclude a majority of structural reverberation noise above it.

Referring to FIG. 2, an adaptive thresholding method is used to binarize the search region (step 26). The objective is to segment the search region by marking each pixel as either "1" if it is inside a cystic structure or "0" if it is not. Assuming that cystic structures are hypoechoic, whereas soft tissues have relatively great pixel intensities, segmentation is achieved by comparing the intensity of each pixel to a threshold. In the simplest implementation, the threshold may be chosen based on some fraction of the global maximum intensity in the search region. For more robust performance, however, an adaptive scheme is also proposed wherein a threshold based on the local pixel intensity distribution is used to classify each pixel.

Figure 4:
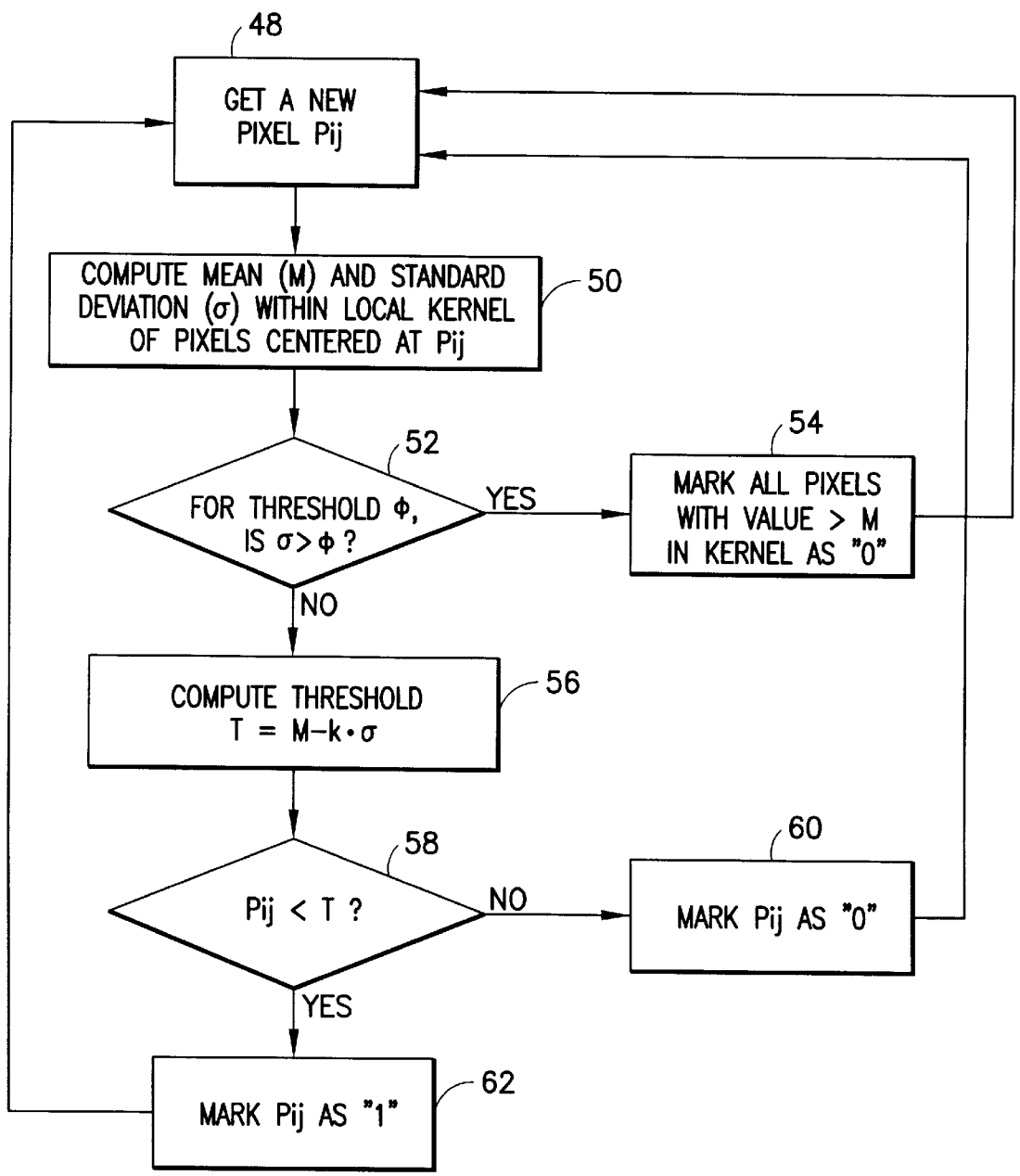
FIG. 4 is a flowchart showing an algorithm for binarization of the search region in accordance with the preferred embodiment of the invention.

While many variations of adaptive thresholding schemes are possible, a preferred binarization method is shown in FIG. 4. For each new pixel $P_{ij}$ in the search region (step 48), we first compute the local mean (M) and standard deviation ($\sigma$) of the neighboring pixels within an R×R kernel centered at pixel $P_{ij}$ (step 50). The kernel size R (e.g., 9) is chosen to be a little smaller than the expected minimum cystic object size.

To test if the kernel contains only tissue speckle and is not inside a cyst, the standard deviation $\sigma$ is compared to a pre-defined threshold value $\phi$ (step 52). If $\sigma > \phi$, the pixels in the kernel are highly unlikely to be "cyst"; however, if the kernel is partially inside a cyst, the condition of $\sigma > \phi$ may still hold. Therefore, only pixels in the kernel with a value greater than the mean (M) are marked as "0" (step 54). If $\sigma < \phi$, an adaptive threshold T is computed (step 56) as follows:

$$T = M - k \times \sigma \quad (1)$$

where k is a constant. In general, k is a small positive fraction such as 0.2.

If $P_{ij} < T$ (step 58 in FIG. 4), then $P_{ij}$ is marked as "0" (not cyst) (step 60); otherwise it is marked as "1" (cyst) (step 62). The same marking step is repeated for each unmarked pixel in the search region (return to step 48).

In general, the binarized image after adaptive thresholding may be very "noisy," consisting of many small, isolated structures. These small structures (mostly speckle noise) can be eliminated by use of morphological filters (step 28 in FIG. 2), which are nonlinear image transformation techniques taught in many digital image processing textbooks (see, e.g., William K. Pratt, Digital Image Processing, 2nd edition, Wiley, New York). Basic morphological operations can be implemented by direct pattern-matching ("hit or miss") transformations, or by using a more efficient pixel stacker and look-up table method.

Erosion and dilation represent two basic morphological operations which, when used in series, can be quite effective in closing up the speckle noise structures. Basically, each pass of an erosion filter strips off the outermost pixel layer of a continuous bright ("1" ) region. This tends to close up the small extraneous bright structures, like speckle noise. The erosion operation will also erode the outermost layer of any cystic region. To offset this undesirable effect, an opposite operation called a dilation, can be applied after each pass of an erosion filter. The effect of a dilation filter is to add back a layer of pixels to existing bright objects. Speckle noise gaps which have been completely closed up (no longer exist) by erosion filtering will not be regenerated by the dilation filter. In practice, one pass of the erosion filter followed by a dilation filter can eliminate a majority of speckle noise structures. But if necessary, additional passes of erosion and dilation can be performed.

Figure 5:
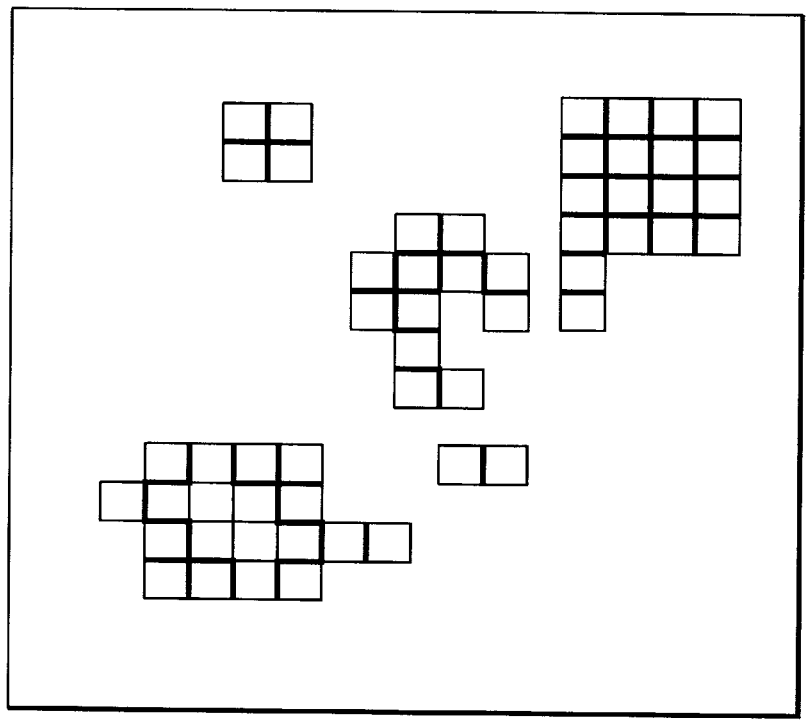
FIG. 5 is a schematic depicting a morphologically filtered search region having a plurality of continuous objects formed by highlighted pixels. The highlighted pixels are "1"s or "cyst"; the background pixels are "0"s.
Figure 6:
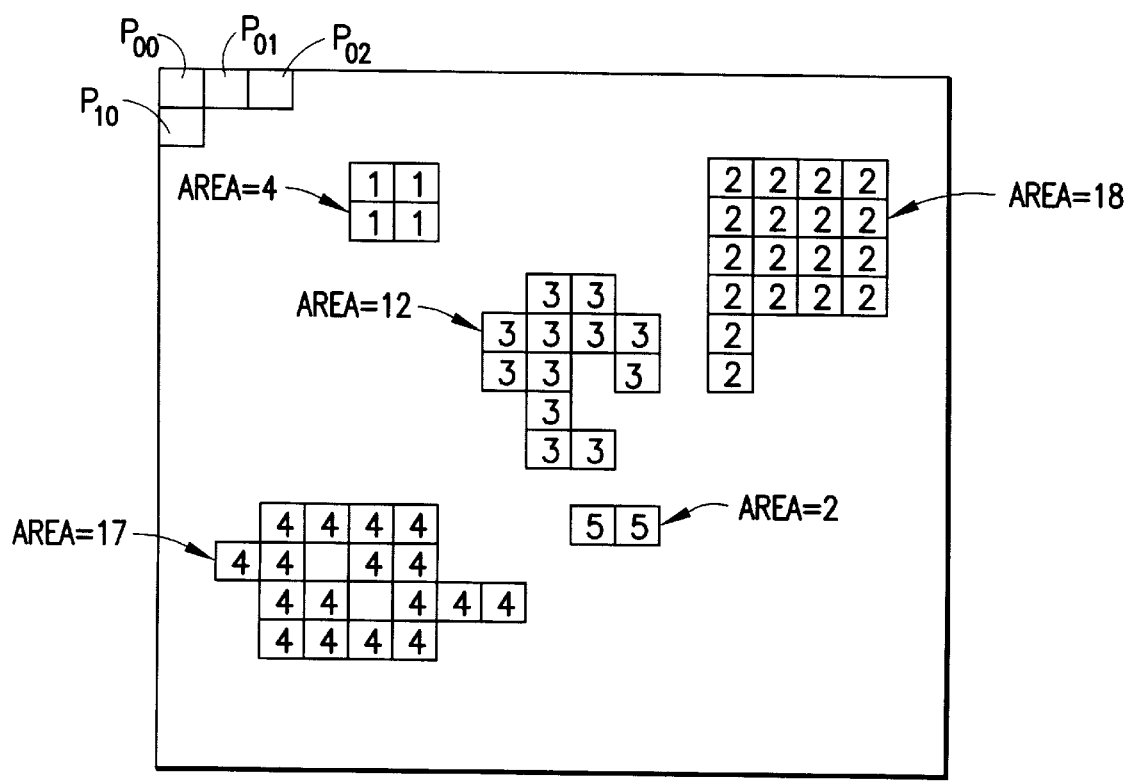
FIG. 6 is a schematic depicting the search region of FIG. 5 after counting of the number of pixels making up each continuous object in accordance with the preferred embodiment of the invention. All pixels of a particular continuous object are assigned an object number, while the algorithm keeps track of the total pixel count (area) of each object.

The aim of step 30 in FIG. 2 is to count the total number of continuous objects in the morphologically filtered search region. A continuous object is defined as a set of object pixels ("1"s) that are connected to each other by pixels within the set. As an example, a search region that consists of five continuous objects is depicted in FIG. 5. In general, a continuous object may contain holes or rough boundary pixel layers with small extrusions. These irregularities can cause confusion during the object segmentation process. Therefore, in accordance with the preferred embodiment of the invention, it is assumed that the objects of interest (cysts) have relatively well-defined shapes without extremely large holes or extrusions. The objective is, as shown in FIG. 6, to segment or group all the object pixels ("1"s) into distinct objects with different object numbers.

A computationally efficient approach that should work well in most situations is the following. Suppose $P_{ij}$ denotes the binarized pixel value in row i and column j. As shown in FIG. 6, beginning from one corner of the search region (e.g., $P_{00}$), the pixels in the image are checked and assigned an object number in a sequential manner as in a raster scan (i.e., row by row). If $P_{ij}=0$ (not cyst), then it remains as zero. If $P_{ij}=1$ (cyst), a predefined kernel of neighboring pixels which have already been scanned, is reviewed. If at least one pixel in this neighborhood kernel is numbered as an object, then the current pixel is considered part of the same object and is assigned the same number. Otherwise, the current pixel is considered the beginning of a new object and is assigned a new object number. The neighborhood kernel consists of pixels in the previous column and/or previous row (which have already been scanned), i.e., pixels in row i, columns j−1, j−2, j−3, . . . , j−n, and row i−1, columns j−1, j, j+1, j+2, . . . , j+m, where n and m are integer values. At a minimum, the pattern should include the three immediate neighbors $P_{i,j-1}$, $P_{i-1,j-1}$, $P^{i-1,j}$, which have already been scanned. The checking of additional pixels in the previous row/columns is recommended to help distinguish between small extrusions and/or broken fragments of an object already numbered and the beginning of a new object.

Having assigned numbers to all of the objects, the total number of objects can be counted easily. Also, as shown in FIG. 6, the area of each object can be computed simply by counting the number of the pixels marked with a given object number.

Referring again to FIG. 2, in step 32 objects that are too large or too small are screened out. Although in step 28 morphological filters were used to remove small speckle-like structures, some of them may still be present in the search region. These small structures will now have unique object numbers, but they can be eliminated by checking if their area is within a predefined range. If the area is smaller than some lower threshold (based on the mean speckle size of the scanner for the current imaging setup), it will be rejected. For example, the two-pixel object (Area=2 pixels) in FIG. 6, which was intended to represent residual speckle noise, will be rejected if the lower threshold is set at Area=3 pixels. If the counted area of an object is too large to be a cyst, the object will also be rejected. Only the remaining objects are considered to be "true" cysts.

Following the rejection of objects having a size outside predetermined limits, the "center of mass" of each remaining object is computed (step 34) using the following equations:

$$x_0 = \frac{\sum_{i=1}^{N} x_i}{N} \quad (2)$$

$$y_0 = \frac{\sum_{i=1}^{N} y_i}{N} \quad (3)$$

In Eqs. (2) and (3), $x_0$ and $y_0$ are the coordinates of the center of mass of the object, N is the number of the pixels comprising the object, and $x_i$ and $y_i$ are the row and column coordinates for pixel $P_{ij}$.

In step 36 the size of each object is measured. For clinical diagnosis, object size is usually characterized in terms of the length of its longest and shortest axes. If the object has an elliptical shape, the longest and shortest axes are orthogonal to one another. To automate this sizing process, a search is conducted for the longest and shortest axes of the object from the center of mass to the boundary pixel of each object. Eight or more search directions with equal angular spacing relative to the center of mass. As an option, if the longest and shortest axes prove to be orthogonal, they can used to draw a fitting ellipse around the object ("cyst"). They can also be used to compute an effective elliptical area of the cyst using the standard area formula for an ellipse. However, as a default, both major (longest) and minor (shortest) axes should be displayed as straight lines (with arrowheads) over the cystic object in the final image (step 38). The center of mass can also be displayed as a cursor on the image. In accordance with the preferred embodiment, the search region is a manually selected rectangular region the boundaries of which are highlighted (e.g., in white) on the displayed image frame. All graphical symbols are generated by the graphics processor in response to instructions from the computer which computes the center of mass and the major and minor axes.

As a final but optional test, the measured lengths of the major and minor axes can also be used to exclude any detected object whose shape is too elongated to be a cyst. That is, if the ratio of the longest to the shortest axis is larger than some predefined threshold, the object is considered suspect and its measurements will not be displayed.

Although the preferred embodiment has been disclosed in the context of an ultrasound imaging system having a host computer and a graphics processor, the functions of both can be performed by one processor. In particular, the functions shown in the flowchart of FIG. 2 can be performed by a single processor. Furthermore, although FIG. 1 shows the architecture of a conventional ultrasound imaging system having multiple processors and a host computer, all of the data processing and computing functions could be performed by a single computer having sufficient processing power.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A method comprising the steps of:
   (a) acquiring a frame of image pixel values;
   (b) binarizing the pixel values within a search region based on a pixel value threshold;
   (c) checking each binarized pixel value within said search region to determine whether said pixel forms part of a continuous object; and
   (d) for each continuous object, assigning an object number to each pixel which is part of the particular continuous object, wherein pixels belonging to the same continuous object are assigned the same object number and pixels belonging to different continuous objects are assigned different object numbers.

2. The method as recited in claim 1, further comprising the step of keeping track of the area of each of said continuous objects.

3. The method as recited in claim 1, further comprising the step of decimating said frame of image pixel values before said binarizing step.

4. The method as recited in claim 1, further comprising the step of applying a smoothing filter to said frame of image pixel values before said binarizing step.

5. The method as recited in claim 1, further comprising the steps of deriving a pixel intensity histogram from said image pixel values and then equalizing said pixel intensity histogram before said binarizing step.

6. The method as recited in claim 1, further comprising the step of defining said search region to exclude an upper band corrupted by near-field reverberation.

7. The method as recited in claim 1, wherein said step of defining said search region to exclude an upper band corrupted by near-field reverberation comprises the step of applying an edge detection filter along a range direction in a portion of said frame.

8. The method as recited in claim 1, further comprising the step of morphological filtering the binarized pixel values to eliminate structures smaller than a speckle size.

9. The method as recited in claim 2, further comprising the step of rejecting continuous objects having a size outside a predetermined size range.

10. The method as recited in claim 1, further comprising the steps of:
    finding a center of mass of at least one of said continuous objects; and
    computing a first dimension of said at least one continuous object relative to said center of mass.

11. The method as recited in claim 10, further comprising the steps of computing a second dimension of said at least one continuous object relative to said center of mass, said first and second dimensions being along mutually perpendicular axes.

12. The method as recited in claim 11, further comprising the step of determining whether a ratio of said first and second dimensions exceeds a pre-defined threshold.

13. The method as recited in claim 10, further comprising the steps of:
    displaying an image derived from said frame of image pixel values; and
    displaying a graphic representing said center of mass superimposed on said image.

14. The method as recited in claim 10, further comprising the steps of:
    displaying an image derived from said frame of image pixel values; and
    displaying a graphic representing said first dimension superimposed on said image.

15. A method comprising the steps of:
    (a) acquiring a frame of image pixel values;
    (b) binarizing the pixel values within a search region based on a pixel value threshold; and
    (c) counting the number of continuous objects in said frame based on binarized pixel values,
    wherein said pixel value threshold is adaptive to local pixel value statistics.

16. The method as recited in claim 15, wherein said binarizing step comprises the steps of:
    computing a local mean and a standard deviation for neighboring pixels within a kernel centered at a pixel;
    computing an adaptive threshold which is a function of said mean and said standard deviation; and
    marking said pixel as being part of a continuous object if the value of said pixel is not less than said threshold.

17. The method as recited in claim 16, wherein said counting step comprises the step of assigning an object number to each pixel marked as being part of a continuous object, wherein pixels belonging to the same continuous object are assigned the same object number.

18. The method as recited in claim 17, further comprising the step of counting the number of pixels marked with a given object number.

19. A system comprising:
    a display device comprising a multiplicity of pixels;
    a memory for storing a frame of image pixel values;
    a computer programmed to perform the steps of:
    (a) controlling said display device to display an ultrasound image derived from said frame of image pixel values;
    (b) binarizing the pixel values within a search region based on a pixel value threshold; and
    (c) counting the number of continuous objects in said frame based on binarized pixel values.

20. The system as recited in claim 19, wherein said computer is further programmed to perform the step of keeping track of the area of each of said continuous objects.

21. The system as recited in claim 19, wherein said computer is further programmed to perform the step of decimating said frame of image pixel values before said binarizing step.

22. The system as recited in claim 19, wherein said computer is further programmed to perform the step of applying a smoothing filter to said frame of image pixel values before said binarizing step.

23. The system as recited in claim 19, wherein said computer is further programmed to perform the steps of deriving a pixel intensity histogram from said image pixel values and then equalizing said pixel intensity histogram before said binarizing step.

24. The system as recited in claim 19, wherein said computer is further programmed to perform the step of defining said search region to exclude an upper band corrupted by near-field reverberation.

25. The system as recited in claim 19, wherein said step of defining said search region to exclude an upper band corrupted by near-field reverberation comprises the step of applying an edge detection filter along a range direction in a portion of said frame.

26. The system as recited in claim 19, wherein said computer is further programmed to perform the step of morphological filtering the binarized pixel values to eliminate structures smaller than a speckle size.

27. The system as recited in claim 20, wherein said computer is further programmed to perform the step of rejecting continuous objects having a size outside a predetermined size range.

28. The system as recited in claim 19, wherein said computer is further programmed to perform the steps of:
finding a center of mass of at least one of said continuous objects; and
computing a first dimension of said at least one continuous object relative to said center of mass.

29. The system as recited in claim 28, wherein said computer is further programmed to perform the steps of computing a second dimension of said at least one continuous object relative to said center of mass, said first and second dimensions being along mutually perpendicular axes.

30. The system as recited in claim 29, wherein said computer is further programmed to perform the step of determining whether a ratio of said first and second dimensions exceeds a pre-defined threshold.

31. The system as recited in claim 28, wherein said computer is further programmed to perform the steps of:
displaying an image derived from said frame of image pixel values; and
displaying a graphic representing said center of mass superimposed on said image.

32. The system as recited in claim 28, wherein said computer is further programmed to perform the steps of:
displaying an image derived from said frame of image pixel values; and
displaying a graphic representing said first dimension superimposed on said image.

33. The system as recited in claim 19, wherein said pixel value threshold is adaptive to local pixel value statistics.

34. The system as recited in claim 33, wherein said binarizing step comprises the steps of:
computing a local mean and a standard deviation for neighboring pixels within a kernel centered at a pixel;
computing an adaptive threshold which is a function of said mean and said standard deviation; and
marking said pixel as being part of a continuous object if the value of said pixel is not less than said threshold.

35. The system as recited in claim 34, wherein said counting step comprises the step of assigning an object number to each pixel marked as being part of a continuos object, wherein pixels belonging to the same continuous object are assigned the same object number.

36. The system as recited in claim 35, wherein said computer is further programmed to perform the step of counting the number of pixels marked with a given object number.

37. The system as recited in claim 19, further comprising:
an ultrasound transducer array comprising a multiplicity of transducer elements;
a transmit beamformer for pulsing selected transducer elements to transmit a series of ultrasound transmit beams in a scan plane;
a receive beamformer coupled to selected transducer elements of said transducer array for acquiring respective receive signals subsequent to respective beam transmits;
a signal processor for forming vectors of image parameter values from said receive signals;
a scan converter for converting said vectors into a frame of image pixel values and storing said frame of image pixel values in said memory; and
a video processor comprising a grayscale mapping for mapping said frame of image pixel values retrieved from said memory into grayscale values.

38. A method comprising the steps of:
(a) acquiring a frame of image pixel values;
(b) binarizing the pixel values within a search region based on a pixel value threshold;
(c) for a first pixel having a first binary value, determining whether at least a second pixel in a kernel of neighboring pixels also has said first binary value; and
(d) assigning the same object identifier to said first and second pixels if both of said first and second pixels have said first binary value.

39. A system comprising:
a display device comprising a multiplicity of pixels;
a memory for storing a frame of image pixel values;
a computer programmed to perform the steps of:
(a) controlling said display device to display an ultrasound image derived from said frame of image pixel values;
(b) binarizing the pixel values within a search region based on a pixel value threshold;
(c) for a first pixel having a first binary value, determining whether at least a second pixel in a kernel of neighboring pixels also has said first binary value; and
(d) assigning the same object identifier to said first and second pixels if both of said first and second pixels have said first binary value.

40. The system as recited in claim 39, wherein said computer is further programmed to perform the step of counting the number of pixels marked with said object identifier.

41. A system comprising:
means for displaying an ultrasound image of tissue;
means for storing a frame of image pixel values from which said ultrasound image was derived; and
a computer programmed to perform the following steps:
binarizing said frame of image pixel values to detect a continuous object; and
computing a center of mass of said continuous object in said image based on the results of binarization.

42. The system as recited in claim 41, wherein said computer is further programmed to compute a distance from said center of mass to a boundary pixel of said continuous object.

* * * * *